Sept. 15, 1936. T. C. KEVITT Plant Pat. 195
GRAPEVINE
Filed Oct. 20, 1934
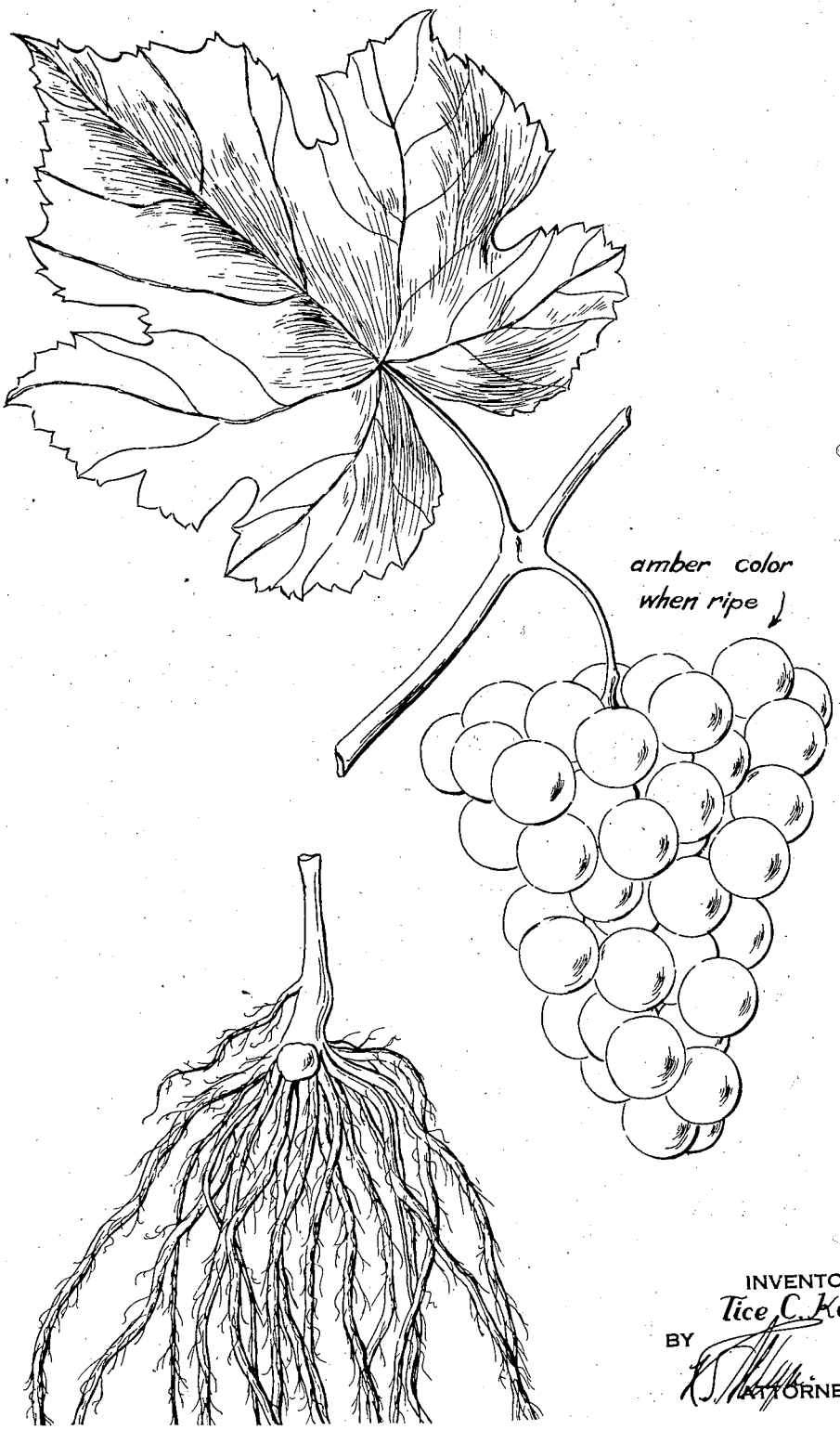
INVENTOR
Tice C. Kevitt
BY
ATTORNEY Patented Sept. 15, 1936

Plant Pat. 195

UNITED STATES PATENT OFFICE

195

GRAPEVINE

Tice C. Kevitt, Pompton Lakes, N. J., assignor to Meyer Aronowitz, doing business as Barclay Nursery, New York, N. Y.

Application October 20, 1934, Serial No. 749,154

1 Claim. (Cl. 47—62)

This invention relates to a grape vine and has for its object to provide a strong and vigorous plant of this sort which bears fruit that is sweet and of superior flavor, firm, of full size and shape, and attractive in appearance.

In 1924 about ten thousand vines were started from the seeds of Niagara grapes at my former nursery in Athenia, New Jersey. Four or five years later and after these vines had borne fruit and had been trimmed and cultivated by me, I selected several vigorous and healthy vines for special care, cultivation, and asexual reproduction and the vine described herein was finally selected as being the most novel, distinctive, attractive and likely to be commercially saleable, of all of said vines.

These vines were cultivated in the vicinity of grape vines of the Brighton and Concord type and it may be that the original variation occurred by reason of the action of insects carrying pollen between the plants.

This vine has been asexually reproduced in the usual manner and the fruit borne by the plant so reproduced by me. The character of soil in which this vine was first grown was medium dark loamy to a depth of about a foot and a half, below which was a stratum of clay to a depth of two to three feet. The fibrous root system formed above the clay.

The drawing illustrates a leaf, a cluster, portions of stem, and roots of the grape vine of this invention.

While grown from the seed of a Niagara grape this vine differs in numerous respects from the Niagara grape vine by being more thrifty and hardy, having fruit that is sweeter when ripe, the vine being more productive. The individual grapes or berries are more nearly round than the Niagara grape and although of the same color before ripening, when ripening the grape of this vine turns a rich golden amber. The clusters are not quite as large as the clusters of the Niagara but are more shouldered while the individual grapes in the cluster are generally larger than the Niagara grape.

The root system is heavier in younger plants than it is in the Niagara vine.

The leaves are deeply notched. The notches are so deep as to almost form five leaves as illustrated instead of one. Under a magnifying glass the leaves may be seen to have fibers closer together and more rugged than the Niagara leaves which is believed to enable them to withstand the attacks of insects and other pests. These leaves are also larger than the Niagara and more leathery and affording better protection to the fruit so that neither the fruit nor leaves are as liable to damage from rain or hail.

The internodes in the vine are more numerous and about twenty-five percent closer together in this vine than in the Niagara with the result that more clusters of fruit are formed and more leaves provided to better protect the fruit from the sun.

The skin of the fruit is thin but tough and less likely to crack and to be attacked by bees than is the skin of the Niagara. The skin as well as the pulp is sweeter than the Niagara grape. The pulp of the fruit underneath the skin is a light green color when ripe.

Under the conditions in which this vine has been grown the grapes ripen some four or five days earlier than the Niagara grapes under similar conditions.

The grape vine shown and described is claimed by me to be distinguished from the Niagara grape vine by the following most important features taken either singly or in combination:

(*a*) This vine is more thrifty and hardy.

(*b*) The fruit is sweeter.

(*c*) Each grape through the entire cluster becomes a rich amber color when ripe, turning from a green color when unripe.

(*d*) It is more productive.

(*e*) The clusters are not quite as large but more shouldered.

(*f*) The individual grapes are a little larger and are much more nearly spherical in shape.

(*g*) The grape of this vine ripens generally four or five days earlier.

(*h*) The root system is heavier in younger plants.

(*i*) The leaves are larger and of the general shape indicated and more deeply notched especially by the four prominent side notches.

(*j*) The leaves are more fibrous, more rugged, more leathery and more numerous.

(*k*) The vine contains more internodes, there being roughly about twenty-five percent more in a given length of vine.

(*l*) The skin of the fruit is also sweeter, yet thin, tough and not as readily adapted to crack open.

Each of these foregoing features I believe and claim to be new in such a type of grape and vine and in combination they specifically define the new variety.

I claim:

A grape vine substantially as shown and described characterized especially by its differences from the Niagara grape, of which it is a new descendant, such differences including a sweeter taste and amber color of the fruit when ripe.

TICE C. KEVITT.